(12) United States Patent
Thakur (10) Patent No.: US 6,685,913 B1
(45) Date of Patent: Feb. 3, 2004

(54) LIPID SOLUBLE RADIOACTIVE METAL CHELATES FOR TUMOR THERAPY

(75) Inventor: Madhukar (Mathew) L. Thakur, Cherry Hill, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/521,767

(22) Filed: Mar. 9, 2000

Related U.S. Application Data
(60) Provisional application No. 60/123,483, filed on Mar. 9, 1999.

(51) Int. Cl.$^7$ ............................................. A61K 51/00
(52) U.S. Cl. ..................................................... 424/1.65
(58) Field of Search ........................ 424/1.65; 534/10; 600/3

(56) References Cited

U.S. PATENT DOCUMENTS

| | | | | |
|---|---|---|---|---|
| 4,017,596 A | * | 4/1977 | Loberg et al. | 424/1.65 |
| 5,130,118 A | * | 7/1992 | Johnson et al. | 424/1.53 |
| 5,972,308 A | | 10/1999 | Dean | 424/1.69 |

OTHER PUBLICATIONS

Silvester, M.R.C.: "Consequences of Indium–111 Decay in Vivo: Calculated Absorbed Radiation Dose to Cells Labelled by Indium–111 Oxine" *Journal Labelled Comp & Radiopharm*, (19), pp. 196–197 (1978).
Thakur, M.L., et al: "Simplified and Efficient Labelling of Human Platelets in Plasma Using Indium–111–2–Mercaptopyridine–N–Oxide: Preparation and Evaluation" *The Journal of Nuclear Medicine*, 26:510–517 (1985).
Hong, et al.: "Radiation toxicity of indium–111–2–mercaptopyridine–N–oxide on HeLa S–3 cells" *The British Journal of Radiology*, 62, 468–472 (1989).
Moerlein, et al.: "The Chemistry of Gallium and Indium as Related to Radiopharmaceutical Production" *International Journal of Nuclear Medicine and Biology*, vol. 8, pp. 277 to 287 (1981).
Matthew L. Thakur: "Live bacteria labeled with $^{111}$In" *European Journal of Nuclear Medicine*, 13:266 (1987).
Thakur, M.L., et al.: "Indium–111 Labeled Platelets: Studies On Preparation And Evaluation Of In Vitro And In Vivo Functions" *Thrombosis Research*, vol. 9, pp. 345–357 (1976).
Howell, Roger W., et al.: "Macrooscopic dosimetry for radioimmunotherapy: Nonuniform activity distributions in solid tumors" *Medical Physics*, vol. 16, No. 1 (1989).
Berge, R.J.M. ten, et al.: "Labeling with Indium–111 has Detrimental Effects on Human Lymphocytes: Concise Communications" *Journal of Nuclear Medicine*, 24:615–620 (1983).

Holman, B. Leonard, et al.: "A New Tc–99m–Labeled Myocardial Imaging Agent, Hexakis(t–Butylisonitrile)–Technetium(1) [Tc–99m TBI]: Initial Experience in the Human" *Journal of Nuclear Medicine*, 25:1350–1355 (1984).
Volkert, W.A., et al.: "$^{99m}$Tc–propylene amine oxime ($^{99m}$Tc–PnAO): a potential brain radiopharmaceutical" *European Journal of Nuclear Medicine* 9:511–516 (1984).
Rosenberg, Steven A. M.D., et al.: "A Progress Report On The Treatment Of 157 Patients With Advanced Cancer Using Lymphokine–Activated Killer Cells And Interleukin–2 Or High–Dose Interleukin–2 Alone" *The New England Journal of Medicine*, vol. 316, No. 15 (1987).
Thakur, M.L., et al.: "Indium–111–Labeled Autologous Leukocytes in Man" *Journal of Nuclear Medicine*, 18:1012–1019 (1977).3
Kelly, J. Duncan, et al.: "Technetium–99m–Tetrofosmin as a New Radiopharmaceutical for Myocardial Perfusion Imaging" *Journal of Nuclear Medicine*, 34:222–227 (1993).
Wang, Shyh–Jen, et al.: "Intratumoral Injection of Rhenium–188 Microspheres into an Animal Model of Hepatoma" *Journal of Nuclear Medicine*, 39:1752–1757 (1998).
Rao, Dandamudi V., et al.: "Cytotoxicity of Some Indium Radiopharmaceuticals in Mouse Tests" *Journal of Nuclear Medicine*, 29:375–384 (1988).
McLean, J.R., et al.: "The Auger Electron Dosimetry of Indium–111 in Mammalian Cells in Vitro" *Radiation Research*, 119, 205–218 (1989).
Thakur, M.L., et al.: "Indium–111–labeled leukocytes for the localization of abscesses: preparation, analysis, tissue distribution, and comparison with gallium–67 citrate in dogs" *The Journal of Laboratory and Clinical Medicine*, St. Louis, vol. 89, No. 1, pp. 217–228 (1977).
Thakur, M.L., et al.: "Indium–111–Labeled Cellular Blood Components: Mechanism of Labeling and Intracellular Location in Human Neutrophils" *Journal of Nuclear Medicine*, 18:1020–1024 (1977).
Pressman, Berton C., et al.: "Molecular and Biological Properties of Ionophores" *American Chemical Society* (1980).
Martell, Arthur E., "Inorganic Chemistry in Biology and Medicine" *American Chemical Society* (1980).

* cited by examiner

*Primary Examiner*—Michael G. Hartley
(74) *Attorney, Agent, or Firm*—Drinker Biddle & Reath LLP (57) ABSTRACT

The present invention is a method of injecting a class of lipid soluble radioactive metal chelate compounds for intratumoral treatment of malignant, benign, metastatic, or inoperable tumors.

7 Claims, 5 Drawing Sheets

(2 of 5 Drawing Sheet(s) Filed in Color)

LIPID SOLUBLE RADIOACTIVE METAL CHELATES FOR TUMOR THERAPY

CROSS REFERENCE TO RELATED APPLICATIONS

This application claims priority under 35 U.S.C. §119 based upon U.S. Provisional Patent Application No. 60/123,483 filed Mar. 9,1999.

FIELD OF THE INVENTION

The present invention generally relates to the field of oncology and a method of injecting radionuclides for tumor therapy, and more particularly to the use of a class of lipid soluble radioactive metal chelate compounds for treatment of malignant, benign, or inoperable tumors.

BACKGROUND OF THE INVENTION

Intratumoral injection of certain radionuclides for therapy is drawing increasing attention. (Shyh-Jen Wang, Wan-Yu Lin, Min-Nan Chen, Ching-Shiang Chi, Jung-Ta Chen, William-L Ho, Bor-Tsung Hsieh, Lie-Hang Shen, Zei-Tsan Tsai, Gann Ting, Saed Mirzadeh and Furn F. Knapp, Jr. Intratumoral Injection of Rhenium-188 Microspheres into an Animal Model of Hepatoma. J Nucl Med 39:1752–1757, 1998). Investigators have begun to use intratumoral therapy, especially where tumors are inoperable or where incision of tumors is associated with high risks to the patient. Radionuclide therapy is particularly useful for treating a variety of tumors, including inoperable tumors; prostate tumors, for example, which are confined but are associated with high risk following surgical intervention; and brain tumors such as glioma.

The use of radioactive metal chelates, in general, and Indium-111 lipid soluble complexes, in particular, is based upon work with such agents in the diagnostic imaging field, especially for labelling cellular blood elements. For example, two of the lipid soluble chelates of Indium-111 have been prepared previously. These compunds are Indium-111-oxine (8-hydroxyquinoline; see M L Thakur, R E Coleman, and M J Welch, Indium-111-labeled leukocytes for the localization of abscesses: preparation, analysis, tissue distribution, and comparison with gallium-67 citrate in dogs. *J Lab Clin Med* 89: 217–228, 1977) and Indium-111-Merc (Mercapto pyridine-N-oxide; see Thakur M L, McKenney S L, Park C H. Evaluation of Indium-111-2-mercaptopyridine-N-oxide (Merc) for labeling leukocytes in plasma: A kit preparation. *J Nucl Med* 26: 518–523, 1982). The lipid soluble nature of these compounds is an important characteristic. When these lipid soluble compounds are placed in the presence of any cell, they are capable of passively diffusing through the cell membrane. As a result, Indium-111-oxine has been used to lable blood cells, bacteria, and tumor cells. (Thakur M L, Lavender J P, Arnot R N, Silvester D J, and Segal A W. Indium-111-Labeled Autologous Leukocytes in Man. *J Nucl Med* 18: 1014–1021, 1977; Thakur M L. Live bacteria labeled with $^{111}$In. *Eur J Nucl Med* 13:266, 1987; Rosenberg S A, Lotze M T, Muul L M, Chang A E, Avis F P, Leitman S, Linehan W M, Robertson C N, Lee R E, Rubin J T, et al. A progress report on the treatment of 157 patients with advanced cancer using lymphokine-activated killer cells and interleukin-2 or high-dose interleukin-2 alone. *NEJM* 316: 889–897, 1987).

A comparison between Indium-111-oxine and Indium-111-Merc has shown that Indium-111-Merc has a higher thermodynamic stability and is smaller in size than Indium-111-oxine. These differences result in the more efficient labeling of cells under physiologic conditions by Indium-111-Merc. Whereas Indium-111-Merc can label cells in the presence of plasma, Indium-111-oxine cannot efficiently label cells unless such cells are suspended in balanced salt solutions, such as isotonic saline. In either case, whether in the oxine or Merc form, once Indium-111 has entered the cells, it firmly binds to cell cytoplasmic components and does not come out of the cells. (See U.S. Pat. No. 4,443,426 by Thakur, Madhukar L.; Thakur, M L and McKenney, S M, Indium 111-mercaptopyridine-N-oxide-labeled human leukocytes and platelets: Mechanism of labeling and intracellular location of $^{111}$In and mercaptopyridine N-oxide, *J Lab Clin Med*, 107:141–147, 1986; Thakur, M L, Segal, A W, Louis, L, Welch, M J, Hopkins J, and Peters, T J, Indium-111-Labeled Cellular Blood Components: Mechanism of Labeling and Intracellular Location in Human Neutrophils, *J Nucl Med*, 18:1020–1024, 1977; Thakur et al., *J Lab Clin Med*, 89: 217–228, 1977).

Through the Auger electrons Indium-111 emits during its decay ($t_{1/2}$=67 hrs), each atom of Indium-111 delivers 0.135 rad of radiation dose to a cell $10\mu$ in diameter. The path range of Auger electrons is 8 to $12.5\mu$. (Silvester, D J, Consequences of Indium-111 decay in vivo; calculated absorbed radiation dose to cells labelled by Indium-111 oxine, *J of Labelled Compounds and Radiopharmaceuticals*, 13: 196–197, 1977). Indium-111 also decays by the emission of two γ-rays of 173 Kev (89%) and 247 Kev (94%). These two γ-rays are useful for scintigraphic imaging.

The present invention takes advantage of the lipid soluble nature of Indium-111 complexes, along with the radioactive properties of these complexes, and utilizes the radioactive metal chelate as a means of treating tumors. The present invention is distinct from receptor-specific agents, such as radiolabeled antibodies or radiolabeled peptides and is distinct from metabolic agents, such as radiodeoxyuridine. By injecting Indium-111-oxine or Indium-111-Merc into a tumor, the Indium-111 atoms enter the tumor cells, bind to tumor cell cytoplasmic components, and deliver high enough radiation dose to the cell DNA such that apoptosis will occur, thereby arresting cell proliferation and/or leading to tumor regression. Chromosomal aberrations in lymphocytes labeled with Indium-111 have been demonstrated. (ten Berge R J M, Natarajhan, A T, Hardeman M R, et al: Labeling with Indium-111 has detrimental effects on human lymphocytes: concise communication. *J Nucl Med* 24:615–620, 1983).

While Indium-111 is one example of an appropriate radioactive metal chelate for tumor therapy, other lipid soluble radioactive chelate could be used, so long as such compounds bind tightly to cell cytoplasmic components. Such alternative lipid soluble compounds include Indium-111-tropolone (2-hydroxy-2,4,6-cylcoheptatrienone), Rhenium-186 or Rhenium-188 chelated with sesta-MIBI (methoxy isobutyl isonitrile), HMPAO, or tetrofosnine. (Holman B L, Jones A G, Lister-James J, et al. A new Tc-99m-labeled myocardial imaging agent, hexakis (tbutylisonitrile) technetium (I) [Tc-99m TBI]: initial experience in the human. *J Nucl Med* 25:1350–1355, 1984; Volkert W A, Hoffman T J, Seger R M, Troutner D E, Holmes R A. $^{99m}$Tc-propylene amine oxime ($^{99m}$Tc-PnAO); a potential brain radiopharmaceutical. *Eur J Nucl Med* 9:511–516 1984; Kelly J D, Forster A M, Higley B, et al. Technetium-99m-tetrofosmin as a new radiopharmaceutical for myocardial perfusion imaging. *J Nucl Med* 34:222–227, 1993).

In addition to inoperable tumors, certain types of prostate tumors, and brain tumors, such radioactive metal chelates could be directed against a variety of other tumors, including hepatoma, melanoma, breast cancer, pancreatic cancer, lung cancer, sarcomas, and carcinoids. Known metastatic tumors can also be treated similarly. The success of the agent used depends upon its homogeneous distribution into the tumor mass. Such a homogeneous distribution is dependent upon the skill and judgment of a physician injecting the agent. As is customary with many therapeutic agents, repeated injections of the agent may be necessary, depending upon the individual patient and the size, location, and type of tumor targeted for therapy. Typically 1mCi of Indium-111 injected into a 1 cc tumor ($1.3 \times 10^{13}$ atom and $10^9$ cells) will deliver 17.5 Gy/cell where distribution of the compound is uniform.

In the present invention, it is important to note that the emission of gamma rays by such radioactive metal chelates may lead to delivery of some radiation to normal organs and tissue within vicinity of the targeted tumor. Such expected radiation dose the normal organs and tissue will have to be determined prior to administration of the therapeutic dose.

Nonetheless, the results of work with the present invention have shown that the radioactivity remains in the tumor and does not spread in the body (22 days observation time); tumor growth is arrested; and treated mammals did not lose body weight when compared to untreated tumor-bearing mammals of the same species.

DEFINITIONS

To arrest tumor cell proliferation means to inhibit cell proliferation, to slow the rate of cell proliferation, to arrest cell proliferation, or to kill tumor cells.

SUMMARY OF THE INVENTION

The present invention is a method of injecting a class of lipid soluble radioactive metal chelate compounds for intratumoral treatment of malignant, benign, metastatic, or inoperable tumors. The present invention also involves a multi-squirter device used to inject the lipid soluble radioactive metal chelate compounds for intratumoral treatment, where the device is designed such that a compound injected with said needle is distributed radially in a uniform volume.

Accordingly, it is an object of the present invention to provide a method of treating a tumor in a mammal, comprising administering a therapeutically effective amount of a lipid soluble radioactive metal chelate to a tumor to arrest tumor cell proliferation.

It is another object of the present invention to provide a method of treating a tumor in a mammal, comprising administering a therapeutically effective amount of a lipid soluble radioactive metal chelate intratumorally to arrest tumor cell proliferation, wherein said radioactive metal chelate is one of the group of Indium-111-oxine, Indium-111-Merc, Indium-111-tropolone, Rhenium-186 HMPAO, Rhenium-188 HMPAO, Rhenium-186 sestaMIBI, or Rhenium-188 sestaMIBI.

It is yet another object of the present invention to provide a method of treating a tumor in a mammal, comprising administering a therapeutically effective amount of a lipid soluble radioactive metal chelate intratumorally to arrest tumor cell proliferation, wherein said lipid soluble radioactive metal chelate consists of a radionuclide from one of the group of Indium-114m, Sn-113, Dy-159, Co-56, Fe-59 Cu-67, Y-90, Ru-97, Ru-103, Pd-103, Cd-115, Sn-117, Te-118, Te-123, Ba-131, Ba-140, Gd-149, Gd-151, Tb-160, Re-186, Re-188, Au-198, or Au-199.

It is another object of the present invention to provide a method of treating a tumor in a mammal, comprising administering a therapeutically effective amount of a lipid soluble radioactive metal chelate intratumorally to arrest tumor cell proliferation, wherein said lipid soluble radioactive metal chelate consists of a chelating agent having a functional group to chelate metal ions with valency states 1 to 7 and said functional group consists of one of the group of OH, NH, $NH_2$, $NO_2$, $N_3$, SH, CO, $PO_4$, CN, NCS, $P_2O_7$, SCN, $S_2O_3$, with donor atoms of C, N, O, P, or S.

It is a further object of the present invention to provide a method of treating a prostate tumor in a mammal, comprising administering a therapeutically effective amount of a lipid soluble radioactive metal chelate to a prostate tumor to arrest prostate tumor cell proliferation.

It is a further object of the present invention to provide a method of treating a prostate tumor in a mammal, comprising administering a therapeutically effective amount of a lipid soluble radioactive metal chelate to said prostate tumor to arrest cell proliferation, where said lipid soluble radioactive metal chelate is Indium-111-oxine.

It is another object of the present invention to provide a method of treating a prostate tumor in a mammal, comprising administering a therapeutically effective amount of a lipid soluble radioactive metal chelate to said prostate tumor to arrest cell proliferation, where said lipid soluble radioactive metal chelate is Indium-111-Merc.

It is another object of the present invention to provide a method of treating an inoperable tumor in a mammal, comprising administering a therapeutically effective amount of a lipid soluble radioactive metal chelate to said inoperable tumor to arrest inoperable tumor cell proliferation.

It is a further object of the present invention to provide a method of treating an inoperable tumor in a mammal, comprising administering a therapeutically effective amount of a lipid soluble radioactive metal chelate to said inoperable tumor to arrest inoperable tumor cell proliferation, where said lipid soluble radioactive metal chelate is Indium-111-oxine.

It is another object of the present invention to provide a method of treating an inoperable tumor in a mammal, comprising administering a therapeutically effective amount of a lipid soluble radioactive metal chelate to said inoperable tumor to arrest inoperable tumor cell proliferation, where said lipid soluble radioactive metal chelate is Indium-111-Merc.

It is another object of the present invention to provide a method of treating a brain tumor in a mammal, comprising administering a therapeutically effective amount of a lipid soluble radioactive metal chelate to said brain tumor to arrest tumor brain tumor cell proliferation.

It is a further object of the present invention to provide a method of treating a brain tumor in a mammal, comprising administering a therapeutically effective amount of a lipid soluble radioactive metal chelate to said brain tumor to arrest brain tumor cell proliferation, where said lipid soluble radioactive metal chelate is Indium-111-oxine.

It is another object of the present invention to provide a method of treating a brain tumor in a mammal, comprising administering a therapeutically effective amount of a lipid soluble radioactive metal chelate to said brain tumor to arrest brain tumor cell proliferation, where said lipid soluble radioactive metal chelate is Indium-111-Merc.

It is another object of the present invention to provide a method of treating a hepatoma in a mammal, comprising administering a therapeutically effective amount of a lipid soluble radioactive metal chelate to said hepatoma to arrest hepatoma cell proliferation.

It is a further object of the present invention to provide a method of treating a hepatoma in a mammal, comprising administering a therapeutically effective amount of a lipid soluble radioactive metal chelate to said hepatoma to arrest hepatoma cell proliferation, where said lipid soluble radioactive metal chelate is Indium-111-oxine.

It is another object of the present invention to provide a method of treating a hepatoma in a mammal, comprising administering a therapeutically effective amount of a lipid soluble radioactive metal chelate to said hepatoma to arrest hepatoma cell proliferation, where said lipid soluble radioactive metal chelate is Indium-111-Merc.

It is another object of the present invention to provide a method of treating a melanoma in a mammal, comprising administering a therapeutically effective amount of a lipid soluble radioactive metal chelate to said melanoma to arrest melanoma cell proliferation.

It is a further object of the present invention to provide a method of treating a melanoma in a mammal, comprising administering a therapeutically effective amount of a lipid soluble radioactive metal chelate to said melanoma to arrest melanoma cell proliferation, where said lipid soluble radioactive metal chelate is Indium-111-oxine.

It is another object of the present invention to provide a method of treating a melanoma in a mammal, comprising administering a therapeutically effective amount of a lipid soluble radioactive metal chelate to said melanoma to arrest melanoma cell proliferation, where said lipid soluble radioactive metal chelate is Indium-111-Merc.

It is another object of the present invention to provide a method of treating a metastatic tumor in a mammal, comprising administering a therapeutically effective amount of a lipid soluble radioactive metal chelate to said metastatic tumor to arrest metastatic tumor cell proliferation.

It is a further object of the present invention to provide a method of treating a metastatic tumor in a mammal, comprising administering a therapeutically effective amount of a lipid soluble radioactive metal chelate to said metastatic tumor to arrest metastatic tumor cell proliferation, where said lipid soluble radioactive metal chelate is Indium-111-oxine.

It is another object of the present invention to provide a method of treating a metastatic tumor in a mammal, comprising administering a therapeutically effective amount of a lipid soluble radioactive metal chelate to said metastatic tumor to arrest metastatic tumor cell proliferation, where said lipid soluble radioactive metal chelate is Indium-111-Merc.

BRIEF DESCRIPTION OF THE DRAWINGS

The file of this patent contains at least one drawings executed in color. Copies of this patent with color drawing(s) will e provided by the Patent and Trademark Office upon payment of the necessary fee.

DETAILED DESCRIPTION

Results with Indium-111 were obtained in mammals by using the following methods:

Tumor-bearing Mice

Four athymic nude mice weighing between 15–18 g were injected intramuscularly in the right flank with approximately $5 \times 10^6$ viable human colorectal carcinoma cells LS174T, human prostate tumor DU145 (male mice), or human breast tumor T74D (female mice). Tumors were allowed to grow to approximately 0.5 cm in diameter.

Preparation of Indium-111-oxine

Indium-111-oxine is available commercially (Amersham Int., Arlington Heights, Ill.). For this procedure, however, Indium-111-oxine was prepared by using a procedure published previously (Thakur M L et al, J Lab Clin Med 89: 217–228, 1977). Indium-111 in chloride form was obtained from MDS Nordion, Vancouver, Canada. Briefly, to the 10 $\mu$l Indium-111-Cl$_3$ Solution (1 mCi, 0.05 N HCl), 1 ml of 0.3 M acetate buffer pH-5.4 was added, followed by 50–100 $\mu$g 8-hydroxyquinoline in 50 $\mu$l ethanol. The reaction mixture was then extracted twice with 1 ml chloroform or methylene chloride. The organic layer was separated each time and combined. Greater than 95% of the activity was extracted. Organic solvent was evaporated, and the residue was taken up in 100 $\mu$l ethanol, which was then diluted to 400 $\mu$l with 0.9% NaCl.

Preparation of Indium-111-Merc (2-Mercaptopyridine-N-oxide)

This was prepared by a method also published previously (Thakur et al J Lab Clin Med 107: 14 1147, 1986; U.S. Pat. No. 4,443,426). As stated previously, this agent, because of its higher thermodynamic stability, does not break down in plasma and passively diffuses into cells in the presence of plasma. Indium-111-oxine is not capable of binding cells in plasma. However, in solid tumors where plasma protein concentration (particularly transferrin, to which Indium-111 binds in plasma) is low, both agents should be equally effective.

The agent was prepared as follows. To one mCi Indium-111-chloride solution in 10 $\mu$l (0.05 M HCl), 150 $\mu$l of 0.05 M phosphate buffer (pH-7.4) was added followed by 50 $\mu$g of Merc in 50 $\mu$l phosphate buffer pH-7.4. This reaction mixture was not extracted in CHCl$_3$ and used as such. Alternatively the resultant complex could also be extracted in chloroform or methylene chloride and be subsequently treated as in the preparation of Indium-111-oxine.

Injecting Agents

On day one, two of the four tumor-bearing mice received a single intratumoral injection of approximately 100 μl Indium-111-oxine. Mice were placed in an ionization chamber, and radioactivity was recorded after the injection and then daily for 28 days. On each day, radioactivity was corrected for decay, and the percent of injected dose retained in the animal was calculated and recorded. Animals were also weighed daily in a calibrated balance.

On day one, all four mice were lightly anesthetized and photographs taken. Mice receiving Indium-111-oxine were also imaged with a gamma camera 28 days later. This qualitatively recorded the distribution of radioactivity, 28 days after it was injected. The control animals received a single intratumoral injection of 100 μl of 25% ethanol in 0.9% NaCl. Two radioactive animals and the control animals were then cared for in two separated cages and allowed to eat and drink at liberty.

On day 22, the two mice treated with Indium-111-oxine received 100 μl of Indium-111-Merc each in two places in tumors. The control animals also received two intratumoral injection of 0.05 M phosphate buffer pH–7.4.

As before, the mice were weighed daily and radioactivity remaining in their bodies was measured for an additional 10 days.

Results

Figure 1:
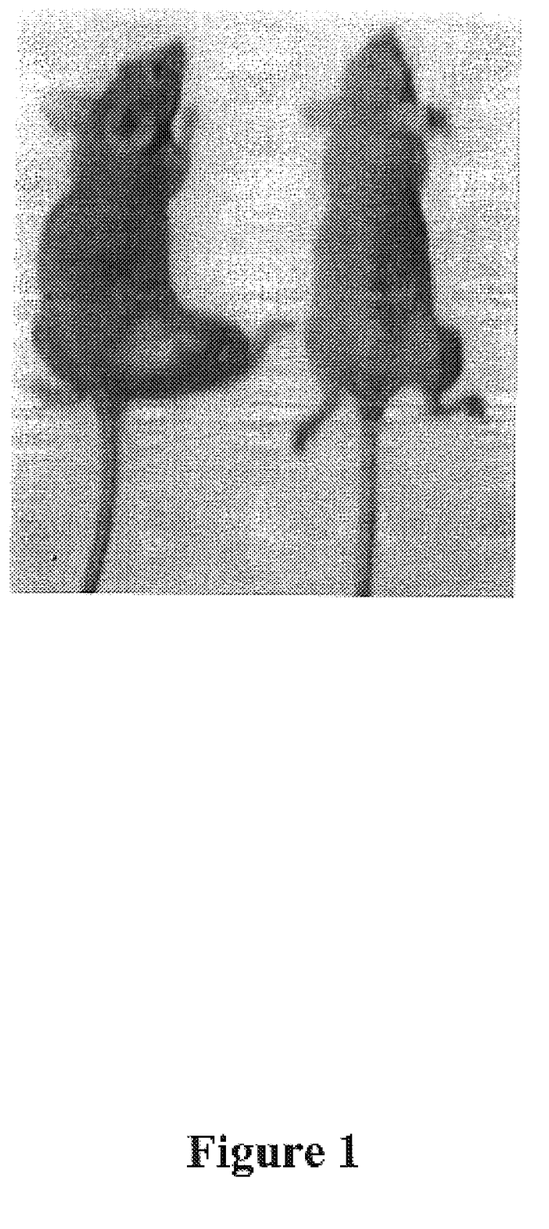
FIG. 1. A polaroid picture of two mice bearing human colorectal cancer (LS174T). The mouse on the right received Indium-111-oxine (648 $\mu$Ci) 22 days previously, and the mouse on the left (control) received only placebo. Excessive tumor growth in the control animal is visible.

FIG. 1 is a photograph of two mice, one receiving Indium-111-oxine (right) and Indium-111-Merc and one from the control group (left), taken on day 22. As can be seen, the tumor in the control mouse at right has grown substantially larger (3.2 cm), but the one in the treated animal has not grown. Results were similar in the remaining two mice.

Figure 2:
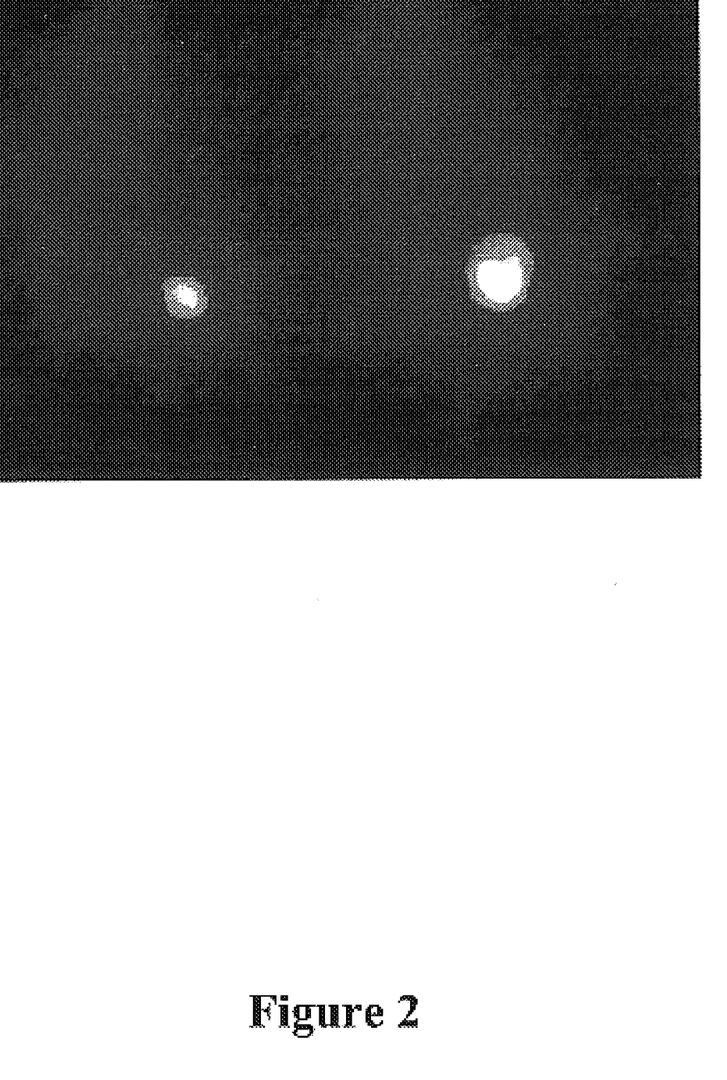
FIG. 2. Posterior gamma camera images of two mice which had received Indium-111-oxine 22 days prior (left) and Indium-111-Merc 10 days prior (right). Images (white spot on the right) show that a major proportion of the radioactivity is still in the tumor.

FIG. 2 shows gamma camera image (left) taken on day 22 after Indium-111-oxine injection. Gamma camera images show that nearly all of the radioactivity was retained in the tumor. Ten days after the injection of Indium-111-Merc, all of the radioactivity was also retained in each animal body (right). Both mice treated with Indium-111 agents had neither gained nor lost body weight. The control animals gained 20.4% and 20.5% body weight.

Figure 3:
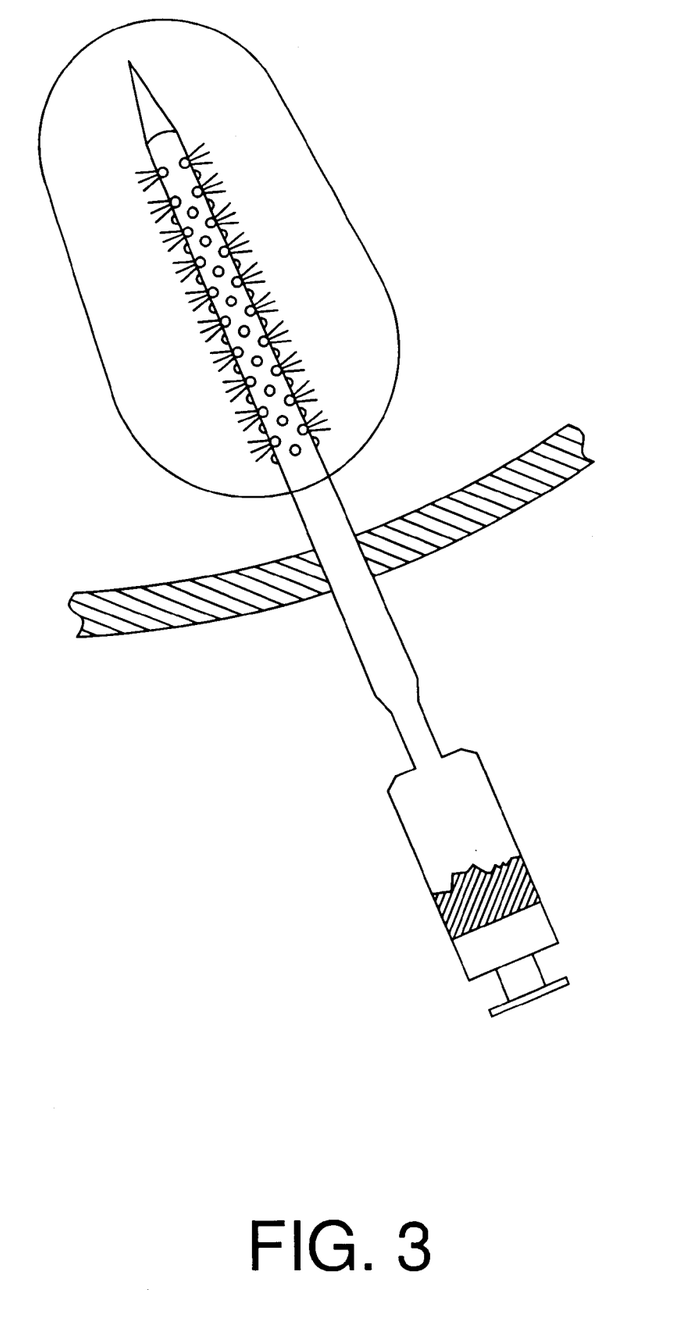
FIG. 3. A schematic drawing of a needle that will permit more homogeneous distribution of radioactivity in the tumor than using a conventional, single, open-ended needle. The end of the needle in question is sharp for penetration but is blocked. The part of the needle has microholes on its surface that will cause a "spray" of the radiaoctive agent, thereby resulting in more homogeneous distribution of the radioactive solution.

FIG. 3 shows a needle designed for intratumoral injection, which will permit more homogeneous distribution of radioactivity in the tumor than by using a conventional needle.

Additional Studies

General Procedures

Additional feasibility studies were performed using two lipid soluble agents, Indium-111-oxine and Indium-111-Mercaptopyridine-N-oxide (Merc). Human prostate and human breast tumors were grown in two separate groups of nude mice. Six mice in each group were divided in two subgroups of 3 mice each. Three mice were treated with intratumoral injections of either Indium-111-oxine or Indium-111-Merc. Each group of mice was then placed in rodent cages separately and cared for with regular diet and water ad lib. Each day the animals were weighed, and tumor diameter was measured three times with a Vernier caliper.

Radioactivity received by each animal was carefully measured, and each day the amount of radioactivity retained in the animal body was measured using an energy calibrated radiation dose calibrator. Two weeks after the first injection, a second dose of the same agent was readministered, also intratumorally and the procedure was followed as described above, for the next two weeks. At the end of this period, the animals were sacrificed, and organs such as the liver, spleen, lungs, kidneys, and bladder were harvested together with the tumor. These organs were then weighed. Indium-111 associated with each tissue was counted, and the radioactivity distributed in each organ was calculated as the percent of the total radioactivity retrained in each animal. Histology on critical organs, such as the liver, bladder, and kidney, as well as tumor histology, was assessed in treated animals and in untreated control animals.

Preparation of Indium-111-oxine

Indium-111 was obtained as a radiochemical in chloride form from MDS Nordion in Canada and converted into Indium-111-oxine using the procedure described previously. (Thakur et al, J Lab Clin Med 89: 217–228, 1977). It should be noted that while studies with Indium-111-oxine have been done previously to assess cytotoxicity, these preparations of Indium-111-oxine were diluted in 0.9% NaCl excessively, stored and used. As a result the compounds obtained in these previous studies were essentially unstable. (See Rao, Sastry, Grimmond, Howell, Govelitz, Lanka and Mylavrapu, Cytotoxicity of Some Indium Radiopharmaceuticals in Mouse Testes, J Nucl Med. (Vol. 29, 1988).

Briefly, to one ml of 0.3 M acetate buffer pH–5.6 were added a required quantity of $^{111}$Indium-Cl$_3$ and 50–100 μg oxine (8-hydroxy quinoline) in 100 μl ethanol. The mixture was vortexed and Indium-111-oxine thus formed was extracted twice with one ml chloroform or methylene chloride. The organic solvent containing greater than 95% of the radioactivity was then separated, and the solvent was evaporated with a gentle stream of nitrogen. After a complete evaporation, 50 μl of ethanol was added followed by 150 μl of 0.9% NaCl. Fifty μl doses were then withdrawn, measured for radioactivity, and administered intratumorally in one or more places. Control animals received a similar volume of 25% ethanol in 0.9% saline in the tumors. Radioactivity received by each animal was then determined by placing the animal in the radioactivity dose calibrator and then measured daily.

Preparation of Indium-111-Merc

Indium-111-Merc was prepared also by a method described previously. (Thakur et al, J Nucl Med 26: 518–523, 1985). Briefly, to one ml 0.067 M phosphate buffer pH 7.4, a required quantity of Indium-111-chloride was added followed by 50 μg Merc in 50 μl 0.067 M phosphate buffer pH 7.4. The reaction mixture was vortexed, and resultant Indium-111-Merc was extracted in chloroform or methylene chloride. This was evaporated to dryness, and the complex was taken up in 50 μl ethanol and 150 μl 0.9% NaCl. A known amount of radioactivity in 50 μl was then injected directly into the tumor in each mouse.

The animals were then treated in the manner described previously.

Preparation of Tumors

Human prostate cancer cells DU145 (5×10$^6$) were implanted in the thigh of nude mice and allowed to grow to less than 0.5 cm in size. These were treated with Indium-111-oxine.

For treatment with Indium-111-Merc, human breast cancer cells (5×10$^6$) T47D were implanted similarly. These were also allowed to grow to up to 0.5 cm in diameter.

Since the principle of this technique is based on intracellular uptake, the type of tumor used does not matter. Tumor vascularity also does not play a major role in performance.

Results

The following are the results from each agent.

Indium-111-oxine

Figure 4:
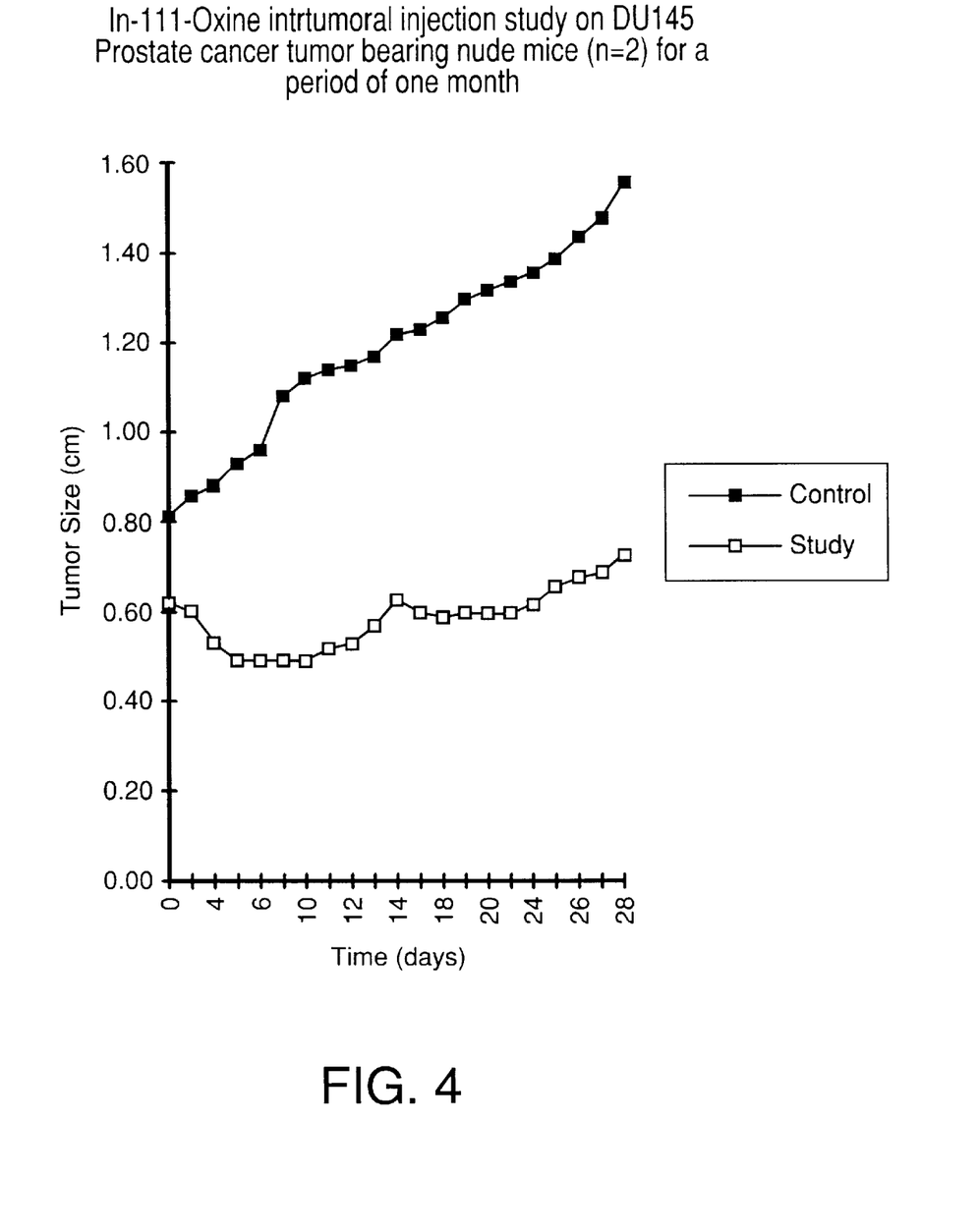
FIG. 4. A graph of tumor size versus time for Indium-111-oxine intratumoral injection study on DU145 human prostate cancer tumor-bearing nude mice (n=2) for a period of one month. The tumor growth in treated mice was arrested, whereas the one in the control mammal continued to grow.

The average radiation dose with Indium-111-oxine received by each animal was estimated to be approximately 131 Gy. The average tumor growth during the treatment period in the treated mice was 117% as compared to 200% in the untreated mice (FIG. 4). On the average, none of the treated or untreated mice either gained or lost body weight. At sacrifice, the tumor retained 86.5% of the injected activity corrected for decay. The kidney uptake was 7.5%, and the liver 5.4%.

Indium-111-Merc

Figure 5:
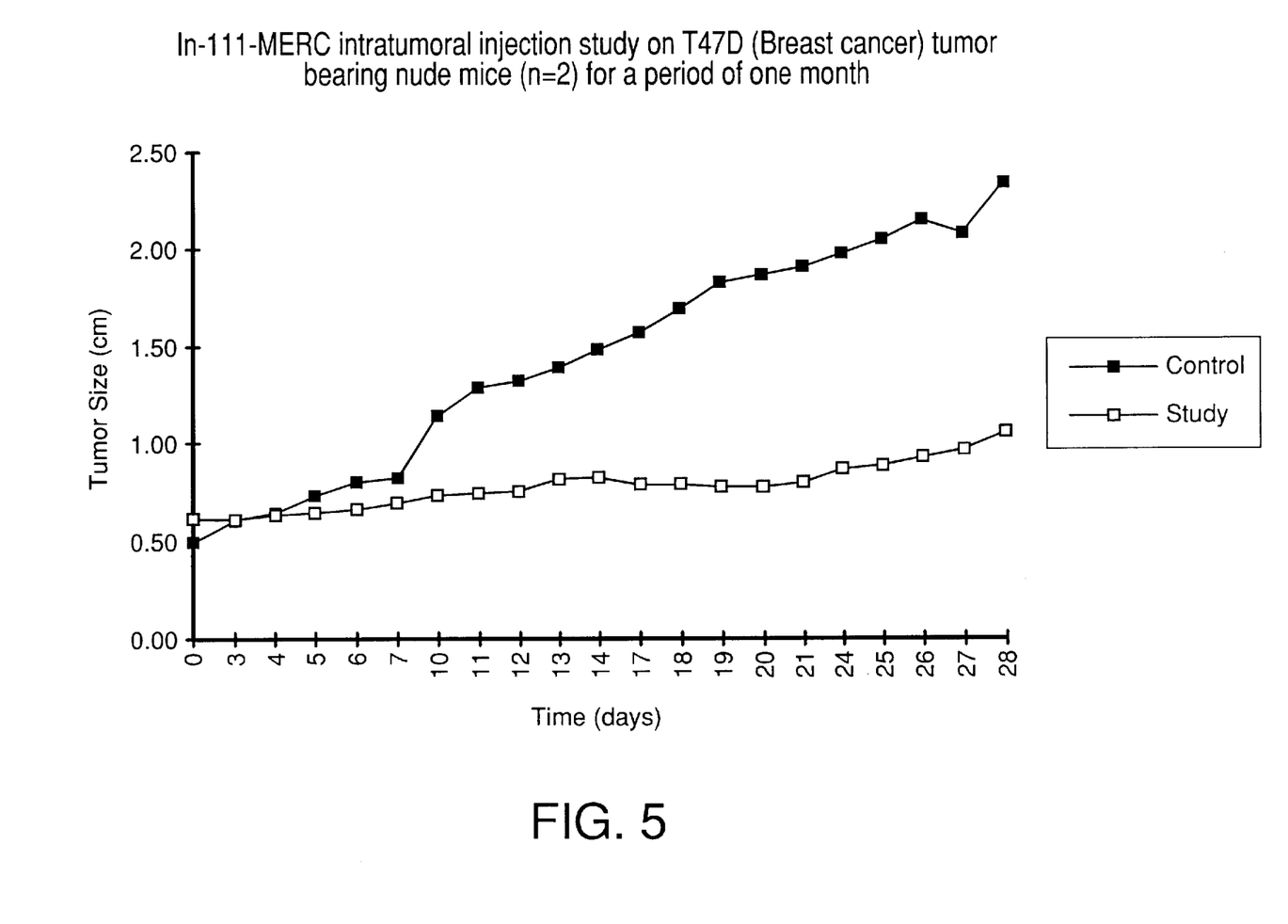
FIG. 5. A graph of tumor size versus time for Indium-111-Merc intratumoral injection study on T47D (human breast cancer) tumor bearing nude mice (n=2) for a period of one month. The tumor growth in treated mice was arrested, whereas the one in the control mammal continued to grow.

The average radiation dose received by animals with Indium-111-Merc was estimated to be approximately 127 Gy. The average tumor growth in the treated mice was 172%, as compared to 477% in the untreated control animals (FIG. 5). All animals gained some body weight. At sacrifice, the Merc treated tumors had retained 92.97% of the injected activity. The kidney had 4.03% and the liver 1.02%.

Histologic Examinations

The histologic examination of treated tumor showed considerable necrotic cells whereas the intact cells were visible in the untreated tumor.

Calculations for Radiation Dosimetry to Tumor and Adjacent Normal Organs

Indium-111 is a cyclotron produced radionuclide that decays by electron capture with a physical half-life of 2.83 d. This decay processes, and the atomic and nuclear transitions that ensue to reach the ground state of $^{111}$Cd, result in the emission of two gamma rays (171 keV-90% and 245 keV-94%), x-rays, 3–27 keV), conversion electrons (145–171 keV-9.7% and 219–245 keV-6.0%), and several Auger electrons (0.5 to 25 keV).

Using the techniques and computer code described by Howell et al. (Howell R W, Rao D V, and Sastry K S R. Macroscopic dosimetry for radioimmunotherapy: Nonuniform activity distributions in solid tumors. *Med Phys* 16: 66–74, 1989), the mean absorbed dose per unit cumulated activity S is 0.01811 rad/$\mu$Ci-hr from $\gamma$ and x-rays (20% of total dose), 0.05776 rad/$\mu$Ci-hr from conversion electrons (64% of total dose) and 0.01502 rad/$\mu$Ci-hr from Auger electrons (16% of total dose), making a total of 0.0909 rad/$\mu$Ci-hr. The cumulated activity $\tilde{A}$ for a 1 mCi intratumoral administration with no biological clearance is 1.44 $A_o$ $T_p$=1.44 (1000 $\mu$Ci) (67.9 h)=9.778×10$^4$ $\mu$Ci-hr. Finally, the mean absorbed dose D=$\tilde{A}$ S=8990 rad per mCi injected.

Using the methods described by Howell et al. (Howell et al. Med Phys 16: 66–74, 1989), we have calculated the absorbed dose profile in a spherical 1 gram tumor (diameter= 1.24 cm) after decay of 1 mCi of In-111 distributed uniformly in the tumor. As indicated above, the mean absorbed dose is 8890 rad per mCi injected. The absorbed dose is somewhat higher at the center of the tumor (9620 rad) and, as expected, drops off to about one-half of that value at the periphery. If it is assumed that the bladder wall is about 0.1 cm from the edge of the tumor, this tissue receives a dose of only about 700 rad. If it is assumed that the rectal wall is 0.3 cm from the edge of the tumor, this tissue only receives a dose of about 400 rad. Therefore the mean absorbed dose to the tumor is 10–20 times higher than the dose to adjacent healthy tissues or the absorbed dose to the adjacent healthy organs is only 5%–10% of the dose to the tumor. This radiation dosimetry compares highly favorably to the brachytherapy in which radiation dose to the bladder and rectal wall are 100% to that of the prostate tumor and to that of the external beam therapy in which, on the average, 25% of the bladder wall and 35% of the rectal wall receive 100% of the dose to the tumor (Waterman F M, Yue N, Corn B W, Dicker A P. Edema associated with I-125 or Pd-103 prostate brachytherapy and its impact on post-implant dosimetry: An analysis based on serial CT acquisition. *Int J Radiat Oncol Biol Phys* 43:447–54, 1999).

Unisquirter System Versus Multisquirter System

In the present system in which tumors are small, and the needle is unisquirter (single outlet), there may not be truly uniform distribution of the radioactivity throughout the tumor. The tumor cells, which receive the radioactivity, cease to grow, but those which did not continue to multiply, thereby causing the slow but continued tumor growth rather than a complete regression. A multi-squirter (multiple outlet) needle can spray the activity in the entire tumor and can produce even better results.

I claim:

1. A method of treating a tumor in a mammal, comprising injecting into a tumor a therapeutically effective amount of a lipid soluble radioactive metal chelate consisting of Indium-111-oxine or Indium-111-merc to arrest tumor cell proliferation.

2. A method of treating a prostate tumor in a mammal, comprising injecting into a tumor a therapeutically effective amount of a lipid soluble radioactive metal chelate consisting of Indium-111-oxine or Indium-111-merc to arrest prostate tumor cell proliferation.

3. A method of treating an inoperable tumor in a mammal, comprising injecting into a tumor a therapeutically effective amount of a lipid soluble radioactive metal chelate consisting of Indium-111-oxine or Indium-111-merc to arrest inoperable tumor cell proliferation.

4. A method of treating a brain tumor in a mammal, comprising injecting into a tumor a therapeutically effective amount of a lipid soluble radioactive metal chelate consisting of Indium-111-oxine or Indium-111-merc to arrest brain tumor tumor cell proliferation.

5. A method of treating a hepatoma in a mammal, comprising administering a injecting into a tumor a therapeutically effective amount of a lipid soluble radioactive metal chelate consisting of Indium-111-oxine or Indium-111-merc to arrest hepatoma cell proliferation.

6. A method of treating a melanoma in a mammal, comprising administering a injecting into a tumor a therapeutically effective amount of a lipid soluble radioactive metal chelate consisting of Indium-111-oxine or Indium-111-merc to arrest melanoma cell proliferation.

7. A method of treating a metastatic tumor in a mammal, comprising administering a injecting into a tumor a therapeutically effective amount of a lipid soluble radioactive metal chelate consisting of Indium-111-oxine or Indium-111-merc to arrest metastatic tumor cell proliferation.

* * * * *